March 12, 1957 F. MEILLAND Plant Pat. 1,576
ROSE PLANT
Filed May 31, 1956
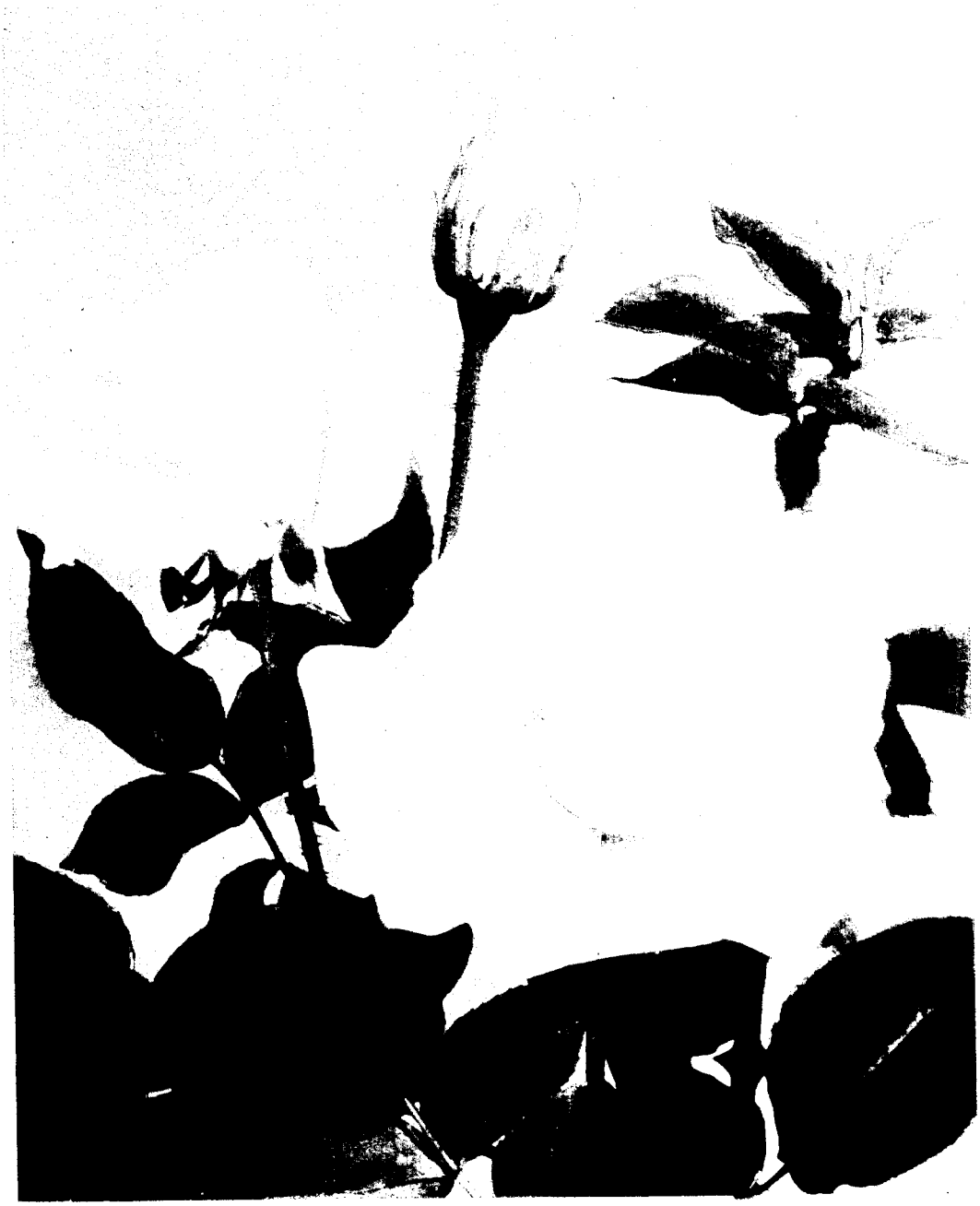
Inventor.
Francis Meilland
By: Robert Robb
Attorneys.

United States Patent Office

Plant Pat. 1,576
Patented Mar. 12, 1957

1,576

ROSE PLANT

Francis Meilland, Cap Azura, France, assignor to The Conard-Pyle Company, West Grove, Pa., a corporation of Pennsylvania Application May 31, 1956, Serial No. 588,594

Claims priority, application France July 29, 1955

1 Claim. (Cl. 47—61)

The present invention relates to a new and distinct variety of rose plant of the hybrid tea class, which was originated by me by crossing the variety "Eclipse" (U. S. Plant Patent No. 172) with the variety "Ophelia" (unpatented).

The primary objective of this breeding was to produce a new rose variety which combines the most desirable characteristics of the parent varieties aforementioned. This objective was fully achieved, as evidenced by the following unique combination of characteristics which are outstanding in the new variety, and which distinguish the new variety from its parents, as well as from all other existing yellow hybrid tea roses:

(1) The free-blooming and exceptionally vigorous habits of growth, with attending tall growth of the plant and a habit of keeping in good balance;

(2) The abundant and attractive foliage;

(3) Unusally good resistance to both mildew and blackspot;

(4) Long, pointed buds of outstandingly good form; and (5) Large blooms of Aureolin Yellow general color tonality, and the very good form of the blooms, with attending greater petalage than the blooms of the present variety "Eclipse."

Asexual reproduction of my new variety by budding, as performed by me in France, and as performed on my behalf at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Outdoor; seedling; for cut flowers and for garden decoration.

Class: Hybrid tea.

Breeding: Seedling.

*Seed parent.*—"Eclipse."

*Pollen parent.*—"Ophelia."

Propagation: Holds its distinguishing characteristics through succeeding propagations by budding.

*Flower*

Locality where grown and observed: West Grove, Pennsylvania, U. S. A.

Flowers Borne: Usually one, sometimes three to stem; on stems of medium length and normal strength.

Quantity of bloom: Abundant, outdoors.

Continuity: Continuous.

Fragrance: Moderate. Nature—Tea.

Bud:

*Peduncle.*—Medium length; medium caliper; stiff; medium roughness; with numerous green hairs. Color—Lettuce Green, Plate 861/1.

*Before calyx breaks.*—Size—medium large. Form—ovoid; with a conspicuous neck; with foliaceous appendages on the surface of the bud; with medium stout, little-cut foliaceous parts extending beyond the tip of the bud equal to ½ or more of its length.

*As calyx breaks.*—Color—Chinese Yellow, Plate 606, streaked with Mandarin Red, Plate 17/1.

*As first petal opens.*—Size—medium. Form—medium length; ovoid. Color: outside—Chinese Yellow, Plate 606, occasionally streaked or washed with Vermillion, Plate 18/1, inside—Chrome Yellow, Plate 605.

*Opening.*—Opens up well.

Bloom:

*Size (when fully open).*—Medium large; from 3½ inches to 4 inches.

*Petalage.*—Double; from 43 to 48 petals.

*Form.*—High-centered at first, but becoming cupped; petals at first being loosely rolled outward, and remaining loosely rolled outward at maturity.

Petals:

*Texture.*—Medium thickness; leathery; with inside satiny and outside velvety.

*Shape.*—Outer petals—obovate; with apex usually coming to a point. Intermediate petals—obovate; usually with 1 notch. Inner petals—obovate; with no notches.

This description of a newly opened flower was made from a rose grown outdoors in the month of September, at West Grove, Pennsylvania, U. S. A.:

*Color.*—Outer petal: outside surface—Aureolin, Plate 3/3 at outer margin, shading to Empire Yellow, Plate 603/1, and then to Aureolin, Plate 3/1 at base, inside surface—Primrose Yellow, Plate 601/3 at outer margin, shading gradually to Aureolin, Plate 3/1. Intermediate petal: outside surface—Straw Yellow, Plate 604/1, shading to Empire Yellow, Plate 603/1, and then to Aureolin, Plate 3/1 at base, inside surface—Aureolin, Plate 3/2, shading to Aureolin, Plate 3/1 at base. Inner petal: outside surface—Straw Yellow, Plate 604/1, shading to Aureolin, Plate 3/1 at base, inside surface—Aureolin, Plate 3/2, sometimes streaked towards base of petal with Buttercup Yellow, Plate 5/1, and shading to Aureolin, Plate 3/1 at base.

This description was made from a rose that was open for 3 days outdoors in the month of September, at West Grove, Pennsylvania, U. S. A.:

*Color.*—Outer petal: outside surface—Canary Yellow, Plate 2/3 at outer margin, shading to Aureolin, Plate 3/2, and then to Aureolin, Plate 3/1 at base; inside surface—Varying from White to Barium Yellow, Plate 503/3 at margin, and shading to Canary Yellow, Plate 2/1 at base. Inner petal: outside surface—Canary Yellow, Plate 2/3 at outer margin, shading to Aureolin, Plate 3/1 at base; inside surface—Naples Yellow, Plate 403/1 at outer margin, shading to Canary Yellow, Plate 2/2 at base.

*General color effect.*—Newly opened flower—Aureolin, Plate 3/1. 3-days open—Canary Yellow, Plate 2/2, showing areas of Aureolin, Plate 3/1.

*Behavior.*—Drop off cleanly; fading to pale yellow; affected by hot weather by tendency to a lightening of tints.

*Flower longevity.*—On bush in garden—4 days in September. Cut roses grown outdoors and kept at living-room temperatures—4 days in September.

*Reproductive organs*

Stamens: Medium number; arranged irregularly about pistils.

Filaments: Many; most with anthers; medium length. Color—Canary Yellow, Plate 2/1.

Anthers: All open at once; medium size; occasionally an anther fused with a petaloid. Color—Canary Yellow, Plate 2/1.

Pollen: Moderate. Color—Lemon Yellow, Plate 4.

Pistils: Medium number.

Styles: Uneven; medium length; medium caliper; bunched.

Stigma: Color—Aureolin, Plate 3/3.

Ovaries: All enclosed in calyx.

Hips: Medium length; ovoid; with inconspicuous neck; smooth; walls thick and dry. Color—green.

Sepals: Permanent; medium length; spear-shaped.

Seeds: Medium number; medium size.

*Plant*

Foliage:

*Leaves.*—Generally 5, but sometimes 3 or 7 leaflets; normal abundance; medium size; leathery.

*Leaflets.*—Shape: lateral—round; terminal—oval. Apex — mucronate. Base — round. Margin—Simply serrate.

*Color.*—Mature: upper surface—Spinach Green, Plate 0960/2; under surface—Willow Green, Plate 000862/1. Young: upper surface—Lettuce Green, Plate 861/1, edged with Oxblood Red, Plate 00823/2; under surface—Lettuce Green, Plate 861/3, lightly overcast with Oxblood Red, Plate 00823/3.

*Rachis (the supporting stem of the compound leaf).*—Medium caliper. Upper side—grooved; hairy. Under side—sparsely prickly.

*Stipules.*—Medium length; moderately narrow; with short points turning out at an angle of more than 45°.

*Disease resistance.*—Unusually good resistance to mildew and blackspot, as determined by comparison with other hybrid tea varieties grown under comparable cultural conditions at West Grove, Pennsylvania, U. S. A.

Growth:

*Habit.*—Bushy; upright; much-branched.

*Growth.*—Free.

*Canes.*—Medium caliper.

*Main stems.*—Color—Willow Green, Plate 00862/1. Thorns—many; from medium length to long; straight; with oval base of medium length. Prickles—none. Hairs—none.

*Branches.*—Color—Spinach Green, Plate 0960/3. Thorns—many; medium length; straight; with oval base of medium length. Prickles—several; brown. Hairs—none.

*New shoots.*—Color—Pod Green, Plate 061. Thorns—several; medium length; straight; with oval base of medium length. Prickles—none. Hairs—none.

I claim:

A new and distinct variety of rose plant of the hybrid tea class, substantially as herein shown and described, characterized particularly as to novelty by its ever-blooming and exceptionally vigorous habits of growth attended by tall plant height and maintenance of good balance, its abundant and attractive foliage, its unusually good resistance to mildew and blackspot, its long and pointed buds of outstandingly good form, its large blooms of Aureolin Yellow general color tonality and their very good form and greater petalage than that of the blooms of the parent variety "Eclipse" (U. S. Plant Patent No. 172).

No references cited.